United States Patent
Houwen et al.

(12)

(10) Patent No.: US 6,225,124 B1
(45) Date of Patent: May 1, 2001

(54) DILUTING REAGENT AND METHOD COMPELLING TIME-INDEPENDENT CONSISTENCY IN MCV ASSAY

(75) Inventors: Berend Houwen, Redlands, CA (US); Kinya Uchihashi, Kakogawa; Yukio Hamaguchi, Akashi, both of (JP); Rolf Mast, Riverside, CA (US)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/323,689

(22) Filed: Jun. 2, 1999

(51) Int. Cl.$^7$ .................................................. G01N 33/48
(52) U.S. Cl. .................... 436/63; 436/8; 436/10; 436/18; 436/176; 436/179; 435/2; 252/408.1
(58) Field of Search ................................. 436/8, 10, 18, 436/63, 70, 174, 176, 179; 435/2; 252/408.1

(56) References Cited

U.S. PATENT DOCUMENTS

| | | | |
|---|---|---|---|
| 4,299,726 | * | 11/1981 | Crews et al. . |
| 4,506,018 | | 3/1985 | North, Jr. ............................. 436/10 |
| 5,116,539 | * | 5/1992 | Hamaguchi et al. .............. 252/408.1 |
| 5,413,938 | * | 5/1995 | Tsujino et al. .......................... 436/63 |
| 5,496,734 | * | 3/1996 | Sakata ..................................... 436/63 |
| 5,618,733 | * | 4/1997 | Sakata et al. .......................... 436/17 |
| 5,888,752 | * | 3/1999 | Malin et al. ........................ 435/7.24 |

FOREIGN PATENT DOCUMENTS

| | | |
|---|---|---|
| 1-33780 | 7/1989 | (JP) . |
| 7-82010 | 9/1995 | (JP) . |
| 8-33388 | 3/1996 | (JP) . |
| 8-122327 | 5/1996 | (JP) . |

OTHER PUBLICATIONS

English abstract of JP96033388, Mar. 29, 1996.*
English abstract of JP08122327, May 17, 1996.*

* cited by examiner

*Primary Examiner*—Maureen M. Wallenhorst
(74) *Attorney, Agent, or Firm*—Shinjyu Intellectual Property Firm

(57) ABSTRACT

Aqueous blood-sample diluting reagent and method of its use for compelling a morphological change in a blood sample to yield an MCV value assayed at elapsed time after the sample is drawn to be consistent within a diagnostically acceptable range with the original, immediate post-drawing MCV value. Selection of a small amount of a predetermined surfactant added within a limited range of concentration, and of a salt for adjusting osmotic pressure of the sample is thereby determined. The blood sample is treated with an anti-coagulant agent immediately post-drawing, and for assay in a particle analyzer at post-drawing elapsed time is diluted with the reagent solution. The reagent has an osmotic pressure ($\pi$) of approximately 150–400 mOsm/kg and a pH of 6.0–8.5. The surfactant is present in a 0.0005% to 0.5% concentration and has a hydrophile-lipophile balance (HLB) of 10–20.

10 Claims, No Drawings

DILUTING REAGENT AND METHOD COMPELLING TIME-INDEPENDENT CONSISTENCY IN MCV ASSAY

BACKGROUND OF THE INVENTION

1. Technical Field

The present invention relates to assaying mean corpuscular volume (MCV) in blood samples; more particularly the invention relates to reagents for, as well as a method of use in, MCV assays using a particle analyzer.

2. Description of Related Art

Automated hematological analyzers are now widely used in the area of clinical examination. As devices for screening patients in medical diagnostic procedures, they are designed for rapid analysis of blood constituents. Such devices can perform the multiple assays of a complete blood count (CBC), including such items as red blood cell (RBC) count, white blood cell (WBC) count, leukocyte classification, hemoglobin concentration (Hb), hematocrit (Ht) and platelet (PLT) count.

The MCV is one among vital items obtained by calculating from these cytometric assay values. The MCV is obtained as the hematocrit divided by the RBC count, that is, the value Ht/RBC, the hematocrit being the percentage of erythrocytes (red blood cells) in a unit volume of whole blood. The MCV, then is the average volume of a single red blood cell, and accordingly it is given in fL, femtoliters, or $10^{-15}$ L.

The hematological analyzers noted above employ flow cytometers. In flow cytometers, a diluted blood sample is discharged into a flow cell at high speed through a very thin nozzle, and the discharging flow from the nozzle is surrounded by the cylindrical flow of a sheathing liquid (laminar flow). By narrowing the laminar flow, the sample flow can thus be focused, to the point at which the flow is essentially a cell-by-cell linear succession. The cells, whose passage in the sample flow is thus controlled by the laminar flow, are then detected optically, by irradiating the flow with a laser beam, as well as electrically, by measuring the resistance or conductivity.

To prepare a whole blood sample for flow-cytometric assay in a hematological analyzer as described above, the sample generally must be treated with an anti-coagulant agent such as an EDTA salt, and diluted with a physiologically isotonic solution.

As diluents for diluting whole blood, there are in general such solutions as physiological saline, Ringer's solution, Locke's solution, and Tyrode's solution. In performing the above-described assays in a hematological analyzer, the foregoing diluents can be used. Ordinarily, however, diluents optimized for individual analyzers are employed.

A basic problem with the current technology in preparing whole blood samples for MCV assay is that the actual MCV changes with post-blood drawing elapsed time. The MCV value that is necessary and important in clinical diagnosis is that which would be obtained immediately after the blood sample is drawn, that is, that value which corresponds to the MCV of the original blood.

In practice, the MCV value as part of a CBC is not measured until as much as 72 hours have passed following drawing of the blood sample. At that point, however, blood samples as such no longer yield suitable MCV assay values. After the blood is drawn, the RBCs in the sample swell, such that MCV values measured with the post-drawing elapse of time are progressively larger than the original RBC mean volume. The original MCV is the actual measurement diagnostically required.

Japanese Pat. Publ. 8-33388 (1996), Japanese Pat. Publ. 7-82010 (1995), and Japanese Laid Open Pat. 8-122327 (1996) disclose various aqueous solutions containing nonionic surfactants. Nevertheless, whichever of these solutions is used as a flow-cytometer sheathing liquid, and the nonionic surfactants are added for eliminating air bubbles within the flow chamber.

Furthermore, Japanese Pat. Publ. 1-33780 (1989) discloses a diluent into which a nonionic surfactant has been added to neutralize the effect on erythrocytes of antiseptic agents, ultimately with the object of restraining post-dilution change in the measured MCV due to the antiseptic agents. Nevertheless, Japanese Pat. Publ. 1-33780 does not disclose a method of restraining change in measured MCV due to the passage time after drawing blood samples.

It would be an important advance in the art if a means could be found to bring about consistency with blood sample original values in hematocrit and RBC count measurements made up to 72 hours after the blood is drawn.

SUMMARY OF THE INVENTION

The present invention compels a blood sample to yield an MCV value assayed at elapsed time after the sample is drawn to be remarkably consistent with the original MCV value of the sample, that is, the immediate post-drawing MCV value.

A reagent in accordance with the invention is a blood sample aqueous diluting solution that includes a small amount of a predetermined surfactant added within a limited range of concentration. The osmotic pressure of the reagent is adjusted with a suitable substance to be within a predetermined range.

A reagent for the present invention is an aqueous solution including a nonionic surfactant, and a salt or suitable substance for adjusting osmotic pressure ($\pi$) to be approximately 150–400 mOsm/kg.

Preferably the osmotic pressure ($\pi$) of the reagent is approximately 230–350 mOsm/kg; especially preferable is an osmotic pressure ($\pi$) of approximately 260–320 mOsm/kg. As examples of nonionic surfactants in an embodiment of the present invention, any of the following can be used.

(1)

(2)

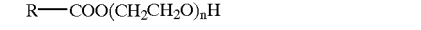

(3)

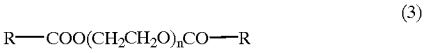

(4)

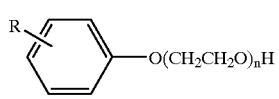

(5)

-continued

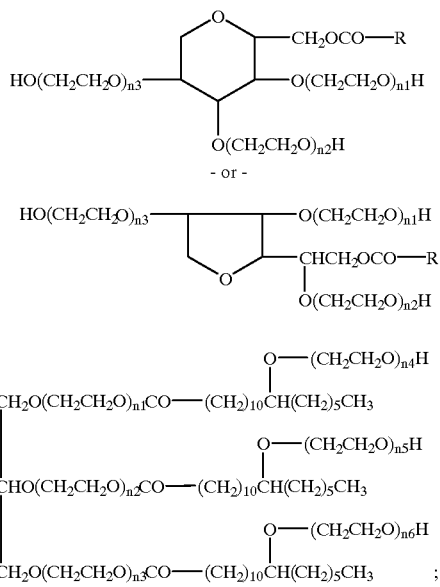

(6)

(7)

wherein R indicates one of an alkyl chain, an alkenyl chain and an alkynyl chain, respectively having 12–24 carbons; and n, $n_1+n_2+n_3$, and $n_1+n_2+n_3+n_4+n_5+n_6$ indicate an integer 5–70.

In a preferred embodiment of the present invention, the nonionic surfactant includes at least one of an alkyl chain, an alkenyl chain and an alkynyl chain, respectively having 12–24 carbons.

The nonionic surfactant preferably includes a polyoxyethylene chain having an ethylene oxide molar addition number of 5–70.

As concrete examples, any of the following nonionic surfactants can be used in an embodiment in accordance with the present invention.

a) Polysorbate-80 (oleate esters of sorbitan plus 20 moles PEG), Croda Co.'s "Crillet 4."
b) Steareth-20 (Stearyl alcohol+PEG 20), Croda Co.'s "Volpo S-20."
c) PEG-60 Almond Glycerides (Almond mono and diglycerides with 60 moles PEG), Croda Co.'s "Crovol A-70."
d) PEG-23 Oleate (oleic acid plus PEG23 ester), Croda Co.'s "Crodet 0 23."

One further preferable nonionic surfactant is Oleth-20 (polyoxyethylene [20] oleyl ether). This surfactant contains a polyoxyethylene oleyl ether mixture wherein the average number of oxyethylene units per molecule is approximately 20.

CTFA Names is the source of the names for the substances noted above.

It should be apparent that within the scope of the present invention, mixtures of nonionic surfactants as herein defined could also be used. It should also apparent that commercially available nonionic surfactants are suitable for this invention, provided that they otherwise conform to the parameters given herein. It is well known that these commercially available nonionic surfactants are not chemically pure materials. Consequently, concomitant introduction of related nonionic structures and extraneous materials into a reagent in accordance with the invention is within its scope, on the condition that the foregoing parameters are satisfied.

It is particularly important that the surfactants or mixtures thereof are transparent in the salt solution. The nonionic surfactants must be completely soluble in water to yield a clear solution at a minimum weight concentration of 0.1%.

The concentration of the given nonionic surfactants for inclusion in the reagent can be suitably determined according to the osmotic pressure and the composition of the salt solution as the solvent. In general, however, the nonionic surfactants can be employed at a low concentration in the range of approximately 0.0005%–0.5%. A preferable concentration is in the range of approximately 0.001%–0.1%, and most preferably is in the range of approximately 0.005%–0.05%.

In accordance with the invention, the nonionic surfactant is used in the salt solution thus designed for diluting and stabilizing blood samples for hematological assay.

The nonionic surfactant preferably has a hydrophile/lipophile (HLB) balance of 10–20.

The pH of a reagent in accordance with the invention is preferably 6.0–8.5.

A reagent given by the present invention further includes a buffer for stabilizing its pH, an additive for adjusting the osmotic pressure of the reagent solution, an antiseptic substance, or an anti-oxidant. Suitable buffers are not particularly limited; however, phosphate buffers, borate buffers, tris buffer, imidazole buffers, etc. are preferable.

Suitable substances for adjusting the pH of the reagent are not particularly limited, but can be, for example, hydrochloric acid or sodium hydroxide.

Suitable substances for adjusting for adjusting the osmotic pressure are not particularly limited. For example, at least one selected from an alkali metal salt or an alkali earth metal salt of sodium chloride, and potassium chloride may be used. Alternatively, a sugar such as sucrose, glucose, etc., or a polyethylene glycol may be used.

A method in accordance with the present invention includes: (a) an anti-coagulant treatment process wherein the blood sample is treated with an anti-coagulant agent; (b) a dilution process wherein the blood sample treated with an anti-coagulant agent is diluted with a reagent solution containing a surfactant to compel a morphological change in red blood cells in the sample, and (c) an assay process wherein the blood sample is assayed in a particle analyzer following the dilution process at the elapse of, for example, at least 48 hours after blood drawing.

In a preferred aspect of the invention, the hematological assay is conducted in a particle analyzer based on the electrical resistance principle; the sheath-flow electrical resistance mechanism is more preferable.

The assay process can be a process wherein the blood sample is assayed in a particle analyzer following said dilution process at the elapse of up to at least 72 hours.

Prior to the assay, whole blood has to be treated with an anti-coagulant agent.

As a standard anti-coagulant treatment, an appropriate amount of an anti-coagulant agent such as EDTA salt is added into a whole blood sample immediately after blood drawing.

The formula of an example anti-coagulant agent is given below.

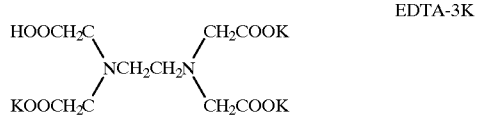

EDTA-3K

The samples are preferably obtained by using a vacuum blood-drawing tube, and preferably are treated with an anti-coagulant agent at the time the blood is drawn.

A diluting solution of the present invention compels morphological changes in blood sample RBCs, and acts on blood samples up to at least 72 hours old accordingly to yield MCV results consistent with those obtained immediately post-drawing.

The action mechanism of the present invention has not been proved. Nevertheless, it was discovered that diluting a blood sample with a solution adjusted to have a predetermined osmotic pressure and containing a predetermined surfactant compels a morphological change in the blood sample RBCs that restores consistency in assayed MCV. The morphological change is to an extent that the MCV value of red blood cells measured at elapsed time post-drawing is equivalent within a diagnostically acceptable range to the MCV value immediately after a blood sample is drawn. Consequently, the present invention provides consistent MCV values throughout the diagnostic life of the blood sample.

This was corroborated by suspending a freshly drawn blood sample as well as a 72-hour old sample into a diluting solution reagent in accordance with the invention, and examining the respective samples microscopically. A similar level of stomatocytes was observed in both samples.

By employing a reagent in accordance with the invention, time-dependent changes in the MCV of a blood sample can be limited. Discrepancies in MCV assayed at different times during the period between when the sample is drawn, and at least 72 hours thereafter, can be controlled to be within about±4(fL), which is well within a diagnostically acceptable range.

The foregoing and other objects, features, aspects and advantages of the present invention will become more apparent from the following detailed description.

DETAILED DESCRIPTION OF EMBODIMENTS

Embodiment 1

Blood samples were treated with EDTA-3K anti-coagulant. The samples were then subjected to an MCV assay in Sysmex Co. Ltd.'s automated hematological analyzer SE-9500 immediately post blood-drawing, and at 72 hours thereafter. The blood samples were stored at 25° C.

Reagent A (Conventional): 15 mM Phosphate Buffer Solution

The osmotic pressure of this reagent was adjusted with sodium chloride to be approximately 250 mOsm/kg, and Reagent B: 15 mM Phosphate Buffer Solution; 0.015% Polyoxyethylene (20) Oleyl Ether The osmotic pressure of this reagent was adjusted with sodium chloride to be approximately 320 mOsm/kg, and its pH was adjusted with sodium hydroxide to be approximately 7.8.

MEAN CORPUSCULAR VOLUME IN FEMOTOLITERS (fL)

| Reagent | Post Blood-Drawing Time | | Variation | Percentage |
|---|---|---|---|---|
| | Immediate | 72 hours | | |
| SAMPLE NO. 1 | | | | |
| Reagent A | 83.8 (fL) | 97.1 (fL) | +13.3 (fL) | +15.9 (%) |
| Reagent B | 88.2 (fL) | 90.4 (fL) | +2.2 (fL) | +2.5 (%) |
| SAMPLE NO. 2 | | | | |
| Reagent A | 89.7 (fL) | 103.9 (fL) | +14.2 (fL) | +15.8 (%) |
| Reagent B | 93.1 (fL) | 96.0 (fL) | +2.9 (fL) | +3.1 (%) |
| SAMPLE NO. 3 | | | | |
| Reagent A | 89.6 (fL) | 103.9 (fL) | +14.3 (fL) | +16.0 (%) |
| Reagent B | 93.9 (fL) | 96.0 (fL) | +2.1 (fL) | +2.2 (%) |

Embodiment 2

Blood samples were treated with EDTA-2K anti-coagulant. The samples were then subjected to an MCV assay in Sysmex Co. Ltd's automated hematological analyzer SE-9500 12 hours and 48 hours post blood-drawing. The blood samples were stored at 25° C.

Reagent A: 15 mM Phosphate Buffer Solution

The osmotic pressure of this reagent was adjusted with sodium chloride to be approximately 250 mOsm/kg, and its pH was adjusted with sodium hydroxide to be approximately 7.8.

Reagent C: 15 mM Phosphate Buffer Solution

The osmotic pressure of this reagent was adjusted with sodium chloride to be approximately 285 mOsm/kg, and its pH was adjusted with sodium hydroxide to be approximately 7.8.

Reagent D: 15 mM Phosphate Buffer Solution; 0.015% Polyoxyethylene (20) Oleyl Ether The osmotic pressure of this reagent was adjusted with sodium chloride to be approximately 285 mOsm/kg, and its pH was adjusted with sodium hydroxide to be approximately 7.8.

MEAN CORPUSCULAR VOLUME IN FEMOTOLITERS (fL)

| Reagent | Post Blood-Drawing Time | | Variation | Percentage |
|---|---|---|---|---|
| | 12 hours | 48 hours | | |
| Reagent A | 93.5 (fL) | 102.6 (fL) | +9.1 (fL) | +9.7 (%) |
| Reagent C | 93.4 (fL) | 103.7 (fL) | +10.3 (fL) | +11.0 (%) |
| Reagent D | 92.7 (fL) | 95.4 (fL) | +2.7 (fL) | +2.9 (%) |

The results indicate that the increase in osmotic pressure of the diluent did not have control over the variation in MCV of the blood samples with post-drawing elapse of time. The addition of nonionic surfactant to the diluent, however, does demonstrate a distinct effect in holding down the variation in MCV.

Embodiment 3

In Embodiment 3, variation in MCV was measured employing reagents prepared from Reagent D by varying its osmotic pressure. The osmotic pressures of the reagents were adjusted by changing the amount of sodium chloride added. The blood samples was stored at 25° C. The samples were assayed in Sysmex Co. Ltd.'s automated hematological analyzer SE-9500 to determine MCV.

| Reagent D: | $\pi$ = 285 mOsm/kg (pH 7.8) |
|---|---|
| Reagent E: | $\pi$ = 250 mOsm/kg (pH 7.8) |
| Reagent F: | $\pi$ = 268 mOsm/kg (pH 7.8) |
| Reagent G: | $\pi$ = 300 mOsm/kg (pH 7.8) |
| Reagent H: | $\pi$ = 320 mOsm/kg (pH 7.8) |

MEAN CORPUSCULAR VOLUME IN FEMOTOLITERS (fL)

| | Post Blood-Drawing Time | | | |
|---|---|---|---|---|
| Reagent | 12 hours | 48 hours | Variation | Percentage |
| | Embodiment 3-1 | | | |
| Reagent A | 94.5 (fL) | 103.7 (fL) | +9.2 (fL) | +9.7 (%) |
| Reagent E ($\pi$ 250) | 93.4 (fL) | 98.3 (fL) | +4.9 (fL) | +5.2 (%) |
| Reagent D ($\pi$ 285) | 92.3 (fL) | 94.2 (fL) | +1.8 (fL) | +2.0 (%) |
| | Embodiment 3-2 | | | |
| Reagent A | 97.4 (fL) | 106.7 (fL) | +9.3 (fL) | +9.5 (%) |
| Reagent F ($\pi$ 268) | 95.4 (fL) | 99.0 (fL) | +3.6 (fL) | +3.8 (%) |
| Reagent D ($\pi$ 285) | 94.1 (fL) | 94.3 (fL) | +0.2 (fL) | +0.2 (%) |
| | Embodiment 3-3 | | | |
| Reagent A | 94.5 (fL) | 103.4 (fL) | +8.9 (fL) | +9.4 (%) |
| Reagent D ($\pi$ 285) | 92.3 (fL) | 95.9 (fL) | +3.6 (fL) | +3.9 (%) |
| Reagent G ($\pi$ 300) | 91.6 (fL) | 95.0 (fL) | +3.4 (fL) | +3.7 (%) |
| Reagent H ($\pi$ 320) | 91.6 (fL) | 93.5 (fL) | +1.9 (fL) | +2.1 (%) |

The results indicate that variation in MCV could be controlled to be within ±4 (fL) by keeping the osmotic pressure of the reagent in the range of 260–320 mOsm/kg. Within this range, higher osmotic pressure demonstrated more control over variation in MCV.

Embodiment 4

In Embodiment 4, variation in MCV was measured employing reagents prepared by adding the nonionic surfactant polyoxyethylene (20) oleyl ether to Reagent A at various concentrations. The blood samples were stored at 25° C. The samples were assayed in Sysmex Co. Ltd.'s automated hematological analyzer SE-9500 to determine MCV.

| Reagent A: | 0.000% nonionic surfactant |
|---|---|
| Reagent E: | 0.015% nonionic surfactant |
| Reagent I: | 0.150% nonionic surfactant |
| Reagent J: | 0.300% nonionic surfactant |

MEAN CORPUSCULAR VOLUME IN FEMOTOLITERS (fL)

| | Post Blood-Drawing Time | | | |
|---|---|---|---|---|
| Conc. (%) | 12 hours | 48 hours | Variation | Percentage |
| Reagent A (0.000%) | 95.8 (fL) | 105.9 (fL) | +10.1 (fL) | +10.5 (%) |
| Reagent E (0.015%) | 95.4 (fL) | 100.0 (fL) | +5.6 (fL) | +5.9 (%) |
| Reagent I (0.150%) | 96.6 (fL) | 100.9 (fL) | +4.3 (fL) | +4.5 (%) |
| Reagent J (0.300%) | 96.2 (fL) | 100.4 (fL) | +4.2 (fL) | +4.4 (%) |

The results indicate that the nonionic surfactant in a wide range of concentrations was relatively effective for controlling variation in MCV.

Embodiment 5

Reagents in Embodiment 5 were prepared by adding approximately 0.015% polyoxyethylene (20) oleyl ether to Reagent E, and then adjusting the osmotic pressure of the diluent to 285 mOsm/kg with the following substances.

| Reagent D: | sodium chloride |
|---|---|
| Reagent K: | sucrose |
| Reagent L: | glucose |
| Reagent M: | polyethylene glycol (MW400) |

The effect on variation in MCV of the foregoing substances employed for adjusting the osmotic pressure of the reagents was measured in Embodiment 5. The blood samples were stored at 25° C. The samples were assayed in Sysmex Co. Ltd.'s automated hematological analyzer SE-9500 to determine MCV.

MEAN CORPUSCULAR VOLUME IN FEMOTOLITERS (fL)

| | Post Blood-Drawing Time | | | |
|---|---|---|---|---|
| Reagent | 12 hours | 48 hours | Variation | Percentage |
| | Embodiment 5-1 | | | |
| Reagent A | 94.7 (fL) | 105.1 (fL) | +10.4 (fL) | +11.0 (%) |
| Reagent D | 92.5 (fL) | 94.8 (fL) | +2.3 (fL) | +2.5 (%) |
| Reagent K | 91.6 (fL) | 94.9 (fL) | +3.3 (fL) | +3.6 (%) |
| Reagent L | 93.0 (fL) | 95.8 (fL) | +2.7 (fL) | +2.9 (%) |
| | Embodiment 5-2 | | | |
| Reagent A | 94.4 (fL) | 104.7 (fL) | +10.3 (fL) | +10.9 (%) |
| Reagent D | 92.8 (fL) | 95.6 (fL) | +2.8 (fL) | +3.0 (%) |
| Reagent M | 92.9 (fL) | 93.6 (fL) | +0.7 (fL) | +0.8 (%) |

The substances employed generally for adjusting osmotic pressure are not limited to those given in Embodiment 5-1 and Embodiment 5-2. The results indicate, however, that salts, sugars and polyethylene glycol are preferable.

While several embodiments have been chosen merely to illustrate the present invention, it will be apparent from this disclosure to those skilled in the art that various changes and modifications can be made herein without departing from the scope of the invention as defined by the appended claims and their equivalents.

What is claimed is:

1. A blood-sample diluting reagent for compelling a volume-stable erythrocyte morphology in a mean corpuscular volume (MCV) assay of drawn blood samples, said reagent being an aqueous solution comprising:

(a). at least one nonionic surfactant present in the aqueous solution in a $5.0 \times 10^{-4}$ to $5.0 \times 10^{-1}$% weight concentration and having a hydrophile/lipophile balance of 10–20, said at least one nonionic surfactant selected to be completely soluble in water to yield a clear solution at a minimum weight concentration of 0.1%, wherein said at least one nonionic surfactant is selected from the group consisting of:

(1)

(2)

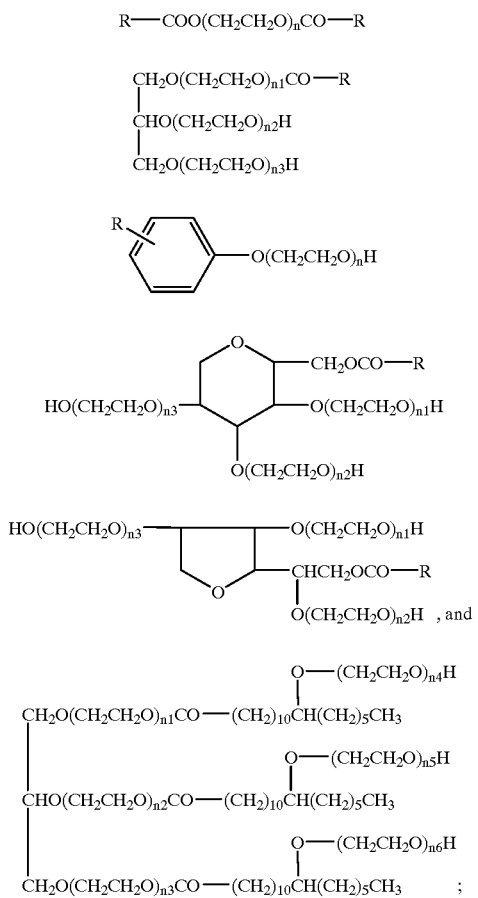

$$R\text{—}COO(CH_2CH_2O)_nCO\text{—}R \quad (3)$$

$$\begin{array}{l} CH_2O(CH_2CH_2O)_{n1}CO\text{—}R \\ | \\ CHO(CH_2CH_2O)_{n2}H \\ | \\ CH_2O(CH_2CH_2O)_{n3}H \end{array} \quad (4)$$

(5) phenyl ring with R substituent and $O(CH_2CH_2O)_nH$ (6) pyranose ring with $HO(CH_2CH_2O)_{n3}$—, $CH_2OCO\text{—}R$, $O(CH_2CH_2O)_{n1}H$, $O(CH_2CH_2O)_{n2}H$ (7) furanose-like ring with $HO(CH_2CH_2O)_{n3}$—, $O(CH_2CH_2O)_{n1}H$, $CHCH_2OCO\text{—}R$, $O(CH_2CH_2O)_{n2}H$, and $$\begin{array}{l} \phantom{CH_2O(CH_2CH_2O)_{n1}CO\text{—}}\!\!O\text{—}(CH_2CH_2O)_{n4}H \\ \phantom{CH_2O(CH_2CH_2O)_{n1}CO\text{—}(CH_2)_{10}}| \\ CH_2O(CH_2CH_2O)_{n1}CO\text{—}(CH_2)_{10}CH(CH_2)_5CH_3 \\ | \phantom{HO(CH_2CH_2O)_{n2}CO\text{—}(CH_2)_{10}}O\text{—}(CH_2CH_2O)_{n5}H \\ CHO(CH_2CH_2O)_{n2}CO\text{—}(CH_2)_{10}CH(CH_2)_5CH_3 \\ | \phantom{CH_2O(CH_2CH_2O)_{n3}CO\text{—}(CH_2)_{10}}O\text{—}(CH_2CH_2O)_{n6}H \\ CH_2O(CH_2CH_2O)_{n3}CO\text{—}(CH_2)_{10}CH(CH_2)_5CH_3 \quad ; \end{array} \quad (8)$$

wherein R indicates one of an alkyl chain, an alkenyl chain and an alkynyl chain, respectively having 12–24 carbons; and n, $n_1+n_2+n_3$, and $n_1+n_2+n_3+n_4+n_5+n_6$ indicate an integer 5–70; and (b) a salt for adjusting osmotic pressure of the aqueous solution to be approximately 150–400 mOsm/kq; whereby the at least one nonionic surfactant and the salt are selected so that discrepancy between MCV values of a freshly drawn blood sample not treated with said reagent and measured immediately post-drawing, and of a freshly drawn blood sample immediately treated with said reagent yet measured up to 72 hours or more post-drawing, is restricted to be within a diagnostically acceptable range.

2. A blood-sample diluting reagent as set forth in claim 1, wherein the osmotic pressure is adjusted to be approximately 230–350 mOsm/kg.

3. A blood-sample diluting reagent as set forth in claim 2, wherein the osmotic pressure is adjusted to be approximately 260–320 mOsm/kg.

4. A blood-sample diluting reagent as set forth in claim 1, wherein said at least one nonionic surfactant is. polyoxyethylne (20) oleyl ether.

5. A blood-sample diluting reagent as set forth in claim 1, wherein said diluting reagent has a pH of 6.0–8.5.

6. A method for mean corpuscular volume (MCV) assay of a drawn blood sample preserved for up to at least 72 hours, the method comprising:

a step of treating said drawn blood sample with an anti-coagulant agent;

a step of diluting said anti-coagulant treated blood sample with a diluting reagent as set forth in claim 1 which compels a morphological change in erythrocytes of said blood sample to yield an MCV value at post-drawing elapsed time to be consistent within a diagnostically acceptable range with immediate post-drawing MCV value of said blood sample; and a step of assaying said blood sample to obtain its MCV value in a particle analyzer.

7. A method for MCV assay as set forth in claim 6, wherein in said step of assaying the blood sample, particle analyzer employs an electrical resistance mechanism.

8. A method for MCV assay as set forth in claim 7, wherein the particle analyzer assays by a sheath flow electrical resistance mechanism.

9. A method for MCV assay as set forth in claim 6, wherein the at least one nonionic surfactant in the diluting reagent is polyoxyethylene (20) oleyl ether.

10. A method for MCV assay as set forth in claim 6, wherein the diluting reagent has a pH of 6.0–8.5.

* * * * *